(12) United States Patent
Clarkson et al.

(10) Patent No.: US 8,765,168 B2
(45) Date of Patent: Jul. 1, 2014

(54) COMPOSITIONS OF A FLUORAPATITE AND METHODS OF USE

(75) Inventors: Brian H. Clarkson, Ann Arbor, MI (US); Kenichi Kuroda, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 82 days.

(21) Appl. No.: 13/505,487

(22) PCT Filed: Nov. 8, 2010

(86) PCT No.: PCT/US2010/055805
§ 371 (c)(1),
(2), (4) Date: Aug. 17, 2012

(87) PCT Pub. No.: WO2011/057180
PCT Pub. Date: May 12, 2011

(65) Prior Publication Data
US 2012/0308622 A1 Dec. 6, 2012

Related U.S. Application Data

(60) Provisional application No. 61/258,905, filed on Nov. 6, 2009.

(51) Int. Cl.
*A61F 13/02* (2006.01)
(52) U.S. Cl.
USPC .................................................. 424/435
(58) Field of Classification Search
CPC ..... A61K 9/006; A61K 6/0032; A61K 6/007; A61Q 11/00; C07C 17/15
See application file for complete search history.

(56) References Cited

U.S. PATENT DOCUMENTS

| 5,139,768 | A | 8/1992 | Friedman |
| 2003/0113686 | A1 | 6/2003 | Jia et al. |
| 2006/0270752 | A1* | 11/2006 | Xu et al. ........................ 523/116 |
| 2006/0292088 | A1 | 12/2006 | Maitra et al. |
| 2007/0258916 | A1 | 11/2007 | Ferracane et al. |
| 2008/0220148 | A1 | 9/2008 | Clarkson et al. |
| 2008/0292088 | A1 | 11/2008 | Beathard et al. |

FOREIGN PATENT DOCUMENTS

| WO | WO-02/22117 A1 | 3/2002 |
| WO | WO-03/000588 A1 | 1/2003 |
| WO | WO-03/008376 A2 | 1/2003 |
| WO | WO-2006/050365 A2 | 5/2006 |

OTHER PUBLICATIONS

Kano et al., "Application of Hydroxyapatite-sol as Drug Carrier", Bio-Medical Materials and Engineering, 4:283-290 (1994).
Abbas et al., Linear and nonlinear viscoelastic analysis of the microstructure of asphalt concretes, J. Mater. Civ. Eng., 16:133-9 (2004).

(Continued)

*Primary Examiner* — Carlos Azpuru
(74) *Attorney, Agent, or Firm* — Marshall, Gerstein & Borun LLP

(57) ABSTRACT

Compositions of fluorapatite derivative crystals are disclosed herein. Also disclosed are methods of using these compositions to treat tooth sensitivity, to use as an anticaries treatment, to use as a restorative material, to use as a tooth surface whitener, and to combat or lessen the side effects of tooth whitening.

11 Claims, 2 Drawing Sheets

(56) References Cited

OTHER PUBLICATIONS

Chen et al., Synthesis of fluorapatite nanorods and nanowires by direct precipitation from solution, Crystal Growth & Design, 6(6):1504-8 (2006).

International Preliminary Report on Patentability from corresponding international application No. PCT/US10/55805, dated May 8, 2012.

International Search Report and Written Opinion from corresponding international application No. PCT/US10/55805, mailing date Jul. 22, 2011.

Lee et al., Synthesis of 3,4-dihydroxyphenylalanine (DOPA) containing monomers and their co-polymerization with PEG-diacrylate to form hydrogels, J. Biomater. Sci., Polymer Ed., 15(4):449-64 (2004).

Macek et al., Viscoelastic analysis of filament-wound composite material systems, J. Reinforced Plastics and Composites, 11:567-81 (1992).

* cited by examiner

COMPOSITIONS OF A FLUORAPATITE AND METHODS OF USE

CROSS REFERENCE TO RELATED APPLICATIONS

The benefit under 35 USC §119(e) of U.S. Provisional Application No. 61/258,905, filed Nov. 6, 2009, is hereby claimed, and its entire disclosure is incorporated by reference herein.

BACKGROUND

Dental enamel is the outermost layer of the teeth. The fully developed mature dental enamel is made of enamel prisms, highly organized micro-architectural units, which have bundles of nanorod-like calcium hydroxyapatite (HA) crystals arranged roughly parallel to each other. This structure spans the entire enamel thickness and is likely to play an important role in determining the unique physico-chemical properties of the enamel.

Dental caries is a widespread, chronic, infectious disease experienced by almost 80% of children in the US by the age of 18 and by more than 90% of adults. Such a phenomenon is not restricted to the U.S., but rather is prevalent throughout the world. Caries is, in fact, considered to have a multifactorial etiology. The most prevalent way in which dentists treat carious tissue is to remove it surgically, resulting in an extensive cavity and loss of structural integrity of the tooth. The current standard of care for carious lesions in the dentin is invasive operative treatment. This means removal of all carious dentin (removal of all diseased tissue) and replacement by a restoration to restore form, function, and integrity of the tooth. The greater number of replacement rather than new restorations also suggests that existing techniques have only limited success and that there will be an ongoing need for restoration of carious lesions, whether primary or secondary in nature. This operative treatment option is time-consuming to both dentists and patients, and costly. Worldwide, the placement, replacement, and repair of restorations in teeth account for anywhere from 30-70% of a dentist's activity. In order to reduce the cost of oral care to both the patient and governmental bodies, there is a need for the development of new anti-caries restorative products and materials.

Dentin hypersensitivity results when protective enamel or cementum covering dentine is lost. Cementum is easier to breach than enamel, because cementum is thinner and more easily eroded by acids. However, breach of cementum cannot happen until there is gingival recession and exposure of the root surface to the oral milieu. Individuals with breached cementum and suffering with dentinal hypersensitivity often experience pain when the exposed area of the tooth comes into contact with cold air or hot and cold liquids or foods that are sweet or acidic or is touched with a metal object.

One way that loss of cementum occurs (and the same is true of enamel) is by the process of dental caries. Acids are produced as end-products of the bacterial degradation of fermentable carbohydrate and these acids dissolve hydroxyapatite, which, like dentin and enamel, is the main calcium phosphate mineral that comprises most of the mineral of the cementum. Another source is acidic foods which, if ingested frequently and for prolonged periods of time, will cause tooth demineralization. These include fruit juices and many beverages, both alcoholic and non-alcoholic. Other acidic agents leading to chemical erosion include various oral personal care products. Amongst these are many of the commercially available mouthwashes and some toothpastes. Abrasive tooth-pastes and vigorous brushing can aid the erosion process. Another way in which dentin tubules lose their protective cementum and enamel coverings is through procedures performed by the dentist or hygienist in the dental office. This includes cavity and crown preparation of teeth for fillings and other restorations. It also includes cementum removal during scaling and root planing by the periodontist or dental hygienist.

Many attempts have been made with limited success to obstruct exposed dentinal tubules and to thereby reduce or stop the ability of stimuli to reach the pulp and cause pain. Materials either singly or in combination have been tried to produce an effective barrier. Blockage of the tubules through the formation of a calcium phosphate precipitate is a common approach. This includes the mixing of a soluble calcium salt with a soluble phosphate salt and immediately applying the combination to the open tubules. Alternatively, application of one salt before the other to try to get a precipitate to form within tubules is also used. There remains acute need for compositions and methods for blocking exposed dentinal tubules to treat dentinal hypersensitivity.

Tooth whitening is of growing popularity, as people become more aware of the importance of white teeth, and the effects that every say diet and activities (such as smoking and wine) have on teeth. One drawback of tooth whitening is that it can cause teeth to become more sensitive, by erosion of cementum, exposing dentin and demineralizing enamel. Sensitivity may be caused by the bleaching agents coming into contact with exposed dentin. Thus, a need exists for a method of combating the side effects of tooth whitening, such as erosion of cementum, softening (demineralization) of enamel and tooth sensitivity.

SUMMARY

Disclosed herein are compositions of apatite derivatives and a carrier, preferably comprising a polymer, where the composition is capable of adhering to wet or dry surfaces, such as a tooth surface. The apatite derivates are crystalline and can have a length of about 500 nm to 20 µm. In some aspects, the crystals have a cross section of about 5 nm to 2 µm. The crystals can be nanorod in shape. The crystals can have a length of about 1 to 2 µm. The crystals can have a cross section of about 10 to about 500 nm. The crystals can be present in the composition in an amount of about 20 to about 40 wt %. The apatite derivative can comprise fluorapatite (FA), hydroxyapatite (HA), or mixtures thereof.

The carrier allows for delivery of the apatite derivative to a surface, such as a tooth surface, and the target site of dentin tubules. The carrier can comprise one or more components, such as polymers, surfactants, lipids, and/or solvents. The polymer can comprise 2-hydroxyethyl methacrylate (HEMA), dihydroxyphenylaalanine (DOPA), alginate, or mixtures thereof. In a preferred embodiment, the polymer comprises HEMA.

In another aspect, provided herein are resin compositions of apatite derivatives and a resin polymer, wherein the apatite derivatives are crystalline and embedded or dispersed throughout the resin polymer. In some cases, the resin polymer is one or more of bisphenol A-glycidyl methacrylate (BIS-GMA), urethane dimethacrylate (UDMA), bisphenol A dimethacrylate (bis-DMA), ethylene glycol dimethacrylate (EGDMA), and triethylene glycol dimethacrylate (TEGDMA). The resin compositions can further include fillers (e.g., silicon dioxide). In various embodiments, the amount of apatite derivative in the resin compositions is 5% wt/vol to 60% wt/vol. In some embodiments, the apatite derivative is silanized. The resin compositions can be used for a variety of applications, including, but not limited to, tooth restorative material, base, cement, sealant, and sealer for root canal work.

Also described herein are methods of using the disclosed compositions comprising applying the composition to the surface of a tooth. The apatite derivative crystals can penetrate the tubules on the tooth surface. The apatite derivative, once applied to the tooth surface, can dissolve or partially dissolve and release one or more ions such as fluoride, phosphate, calcium, and/or carbonate. In some cases, fluoride, phosphate, and calcium are released. In various cases, released calcium and/or phosphate ions then redeposit onto the tooth surface. The composition can adhere to the tooth surface even when the tooth surface is wet.

Application of the composition to the tooth surface can be by rubbing the composition on the tooth surface. Additionally or alternatively, the composition can be applied by brushing, wiping, patting, or coating the composition on the surface of the tooth. The application of the composition onto the tooth surface can be weekly, repeated daily, or repeated twice daily.

Application of the composition to the tooth surface can be to reduce tooth sensitivity, to prevent or retard dental caries, and/or to reduce side effects due to tooth whitening procedures, such as erosion of cementum and/or dentin or softening of enamel.

In yet another aspect, the compositions as disclosed herein can be used as a cosmetic tooth varnish, whereby the composition is applied to the surface of the tooth to whiten the tooth, similar as painting a nail with nail polish. In some specific cases, the compositions further comprise one or more other colorants or additives to affect the color of the composition. One example is titanium dioxide. Other colorants can be added to match the color of the composition to the color of a tooth.

DETAILED DESCRIPTION

Figure 1:
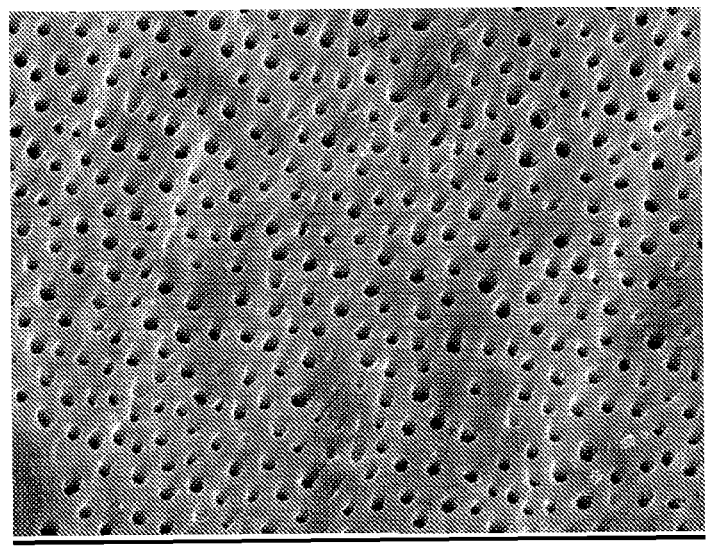
FIG. 1 shows a scanning electron microscopy image of dentin tubules on the surface of teeth, after being etched with ethylenediaminetetraacetic acid for 3 minutes.

Disclosed herein are compositions of an apatite derivative and methods of using these compositions. The compositions disclosed herein are useful in a variety of dental applications, such as to reduce tooth sensitivity, to treat caries, to treat or prevent erosion of dental hard tissues, to reduce the side effects of tooth whitening, and/or to provide temporary tooth whitening as a tooth varnish.

In some aspects, the compositions disclosed herein comprise an apatite derivative and a carrier with viscoelastic gel properties. Viscoelastic gels are gels having both viscous and elastic properties. Assessment of such properties of any given composition can be performed using known techniques. See, e.g., Abbas, et al., *J. Mat. Civil Eng.,* 16:2 133-139 (2004), or Macek, et al. *J Reinforced Plastics Composites,* 11:567-581 (1992).

The compositions can be paste-like or a gel-like consistency. This consistency allows for easy application to tooth surfaces, and furthermore, allows for the composition to stay on the surface sufficient time to allow for deposit of the apatite derivative onto and into the tooth surface, into by means of penetrating into mature (hard), softened, or eroded enamel, dentin, and/or cementum surfaces and the dentin tubules. The compositions preferably can adhere to the surface of a tooth without need of drying the tooth prior to application of the composition. In some cases, the composition is a viscoelastic gel composition, having both viscous and elastic properties. Some non-limiting examples include carbopol, poloxamers, and polyethylene glycol (PEG).

The carrier of the composition can comprise one or more components, such as polymers, surfactants, lipids, and/or solvents. The carrier, or carriers, present in the compositions disclosed herein are selected to provide a viscosity to the composition so the composition adheres to the tooth surface.

The carrier preferably comprises a polymer. Polymers are added as a component to the disclosed compositions to facilitate the compositions' adhesion to the tooth surface. Polymers of (1) a glycolic acid, glycerin, or derivatives thereof and (2) an oxide, such as calcium oxide, have high shear attachment strength, such as at least 200 kPa or up to 500 kPa, which facilitate adhesion of the compositions disclosed herein to tooth surface. Such mixtures can produce a gel in a matter of minutes with a stability of 10-14 days, in an oral environment.

The polymers used herein can be any polymer suitable for forming a viscoelastic gel and compatible with applications to a tooth, e.g., approved for use on or in the human body. Nonlimiting examples of polymers contemplated include hydroxyethyl methacrylate (HEMA), dihydroxyphenylanaine (DOPA) containing polymers, and alginate. Other polymers contemplated include polysaccharides, polyethylene glycol, polyvinyl alcohol. DOPA polymers are described in Lee, et al., *J. Biomater. Sci. Polymer Edn.,* 15:449-464 (2004) and WO 03/008376, each of which is incorporated by reference in its entirety. In some cases, the polymers used herein are water soluble.

The polymers used herein can be of any molecular weight, but preferably are of a molecular weight sufficient to provide a film or coating on the tooth. Additives can be added to the polymers to control the morphology and/or viscosity of the polymers. For example, alginate polymers can form hydrogels with the addition of a calcium salt. Polyvinyl alcohols can form gels with the addition of a borate salt.

Suitable surfactants include Triton X-100, docusate sodium salt (AOT), sodium dodecyl sulfate (SDS), cetyltrimethyl ammonium bromide (CTAB), polysorbates, e.g. polysorbate 20 or polysorbate 80, poloxamers, e.g., polyxamer 188 or 184, polyoxyethylene derivatives, polyoxypropylene derivatives, and sodium monolaurate. Non-limiting examples of known nonionic surfactants include aliphatic, primary or secondary linear or branched chain alcohols or phenols with alkylene oxides, generally ethylene oxide and generally 6-30 ethylene oxide groups. Other surfactants include mono- or di-alkyl alkanolamides, alkyl polyglucosides, and polyhydroxy fatty acid amides. Non-limiting examples of known anionic surfactants include the sodium, ammonium, and mono-, di-, and tri-ethanolamine salts of alkyl sulfates, alkyl ether sulfates, alkaryl sulfonates, alkyl succinates, alkyl sulfosuccinate, N-alkoyl sarcosinates, alkyl phosphates, alkyl ether phosphates, alkyl ether carboxylates, and α-olefin sulfonates. The alkyl groups generally contain from 8 to 18 carbon atoms and may be unsaturated. The alkyl ether sulfates, alkyl ether phosphates, and alkyl ether carboxylates may contain from 1 to 10 ethylene oxide or propylene oxide units per molecule, and preferably contain 2 to 3 ethylene oxide units per molecule. Known anionic surfactants include sodium or ammonium lauryl sulfate and sodium or ammonium lauryl ether sulfate. Non-limiting examples of known amphoteric surfactants include alkyl amine oxides, alkyl betaines, alkyl amidopropyl betaines, alkyl sulfobetaines, alkyl glycinates, alkyl carboxyglycinates, alkyl amphopropionates, alkyl amidopropyl hydroxysultaines, acyl taurates, and acyl glutamates wherein the alkyl and acyl groups have from 8 to 18 carbon atoms.

Solvents used herein can include water, ethyl alcohol, isopropyl alcohol, glycerin, propylene glycol, acetone, and mixtures thereof. Lipids used herein include phospholipids, fatty acids, steroids (e.g., cholesterol), and mixtures thereof.

In some other aspects, the compositions disclosed herein are resin compositions and comprise an apatite derivative and a resin polymer. Resin polymers include one or more of bisphenol A-glycidyl methacrylate (BIS-GMA), urethane dimethacrylate (UDMA), bisphenol A dimethacrylate (bis-DMA), ethylene glycol dimethacrylate (EGDMA), and triethylene glycol dimethacrylate (TEGDMA). The resin compositions can further include fillers (e.g., silicon dioxide). In some embodiments, the apatite derivative is silanized. These resin compositions can be used in a variety of dental applications, including as tooth restorative materials, as a base material in dental reconstruction or other reconstruction, as a cement, as a sealant, and/or as a sealer for root canal work.

Other components contemplated for the compositions disclosed herein include salts, oxides, and hydroxides, such as, but not limited to, sodium, potassium, calcium, and magnesium oxides, hydroxides, acetates, acrylates, glutarates, methacrylates, and the like.

As used herein, the term "apatite derivative" refers to hydroxyapatite (HA) ($Ca_{10}(PO_4)_6(OH)_2$), fluorapatite (FA), carbonated hydroxyapatite, carbonated fluorapatite, and mixtures thereof. In some embodiments, the apatite derivative can be silanized.

The apatite derivative is present in the composition or resin composition at a weight percent of about 5 to about 60 wt %. In some cases, the apatite derivative comprises FA, consists essentially of FA, or consists of FA. In some other cases, the apatite derivative comprises HA, consists essentially of HA, or consists of HA. The amount of apatite derivative can be present in the disclosed compositions at about 20 to about 60 wt %, about 20 to about 50 wt %, about 20 to about 40 wt %, about 20 to about 30 wt %, or about 30 to about 40 wt %. Also contemplated are amounts of apatite derivative of about 5, about 10, about 15, about 20, about 25, about 30, about 35, about 40, about 45, about 50, about 55, and about 60 wt %.

The apatite derivatives used herein are crystalline, and can have a nanorod shape. The crystals can have a length of about 500 nm to about 20 μm and a cross section of about 10 nm to about 3 μm. In some cases, the crystals have a length of about 500 to about 5 μm, or about 1 to about 2 μm. In various cases, the crystals have a cross section of about 10 to about 500 nm, about 10 to about 200 nm, about 20 to about 150 nm, about 20 to about 100 nm, about 20 to about 50 nm, or about 30 to about 40 nm. In other cases, the crystals have a cross section of about 2 to about 3 μm. In a specific case, the crystals have a length of about 500 nm to about 2μ and a cross section of about 50 to about 500 nm. Methods of preparing apatite derivative crystals are known in the art, e.g., WO 06/050365, which is herein incorporated by reference in its entirety.

Other additives may also be included in the present composition to enhance its appeal. For example, flavoring agents based on oils of spearmint and peppermint may be added to the composition to provide a desirable tasting composition. Other compounds which may be used to provide a composition with an appealing flavor include menthol, clove, wintergreen eucalyptus and aniseed. An amount of flavoring agent suitable for inclusion in the present composition may be in the range of about 0.1 to about 5 wt %. Sweetening agents may also be added to the present composition. Examples of suitable sweetening agents include, but are not to be limited to, saccharin, sodium cyclamate, aspartame, xylitol and sucrose. Sweetening agents generally comprise about 0.1 to about 5 wt %. Colorant such as titanium dioxide, antioxidants such as ascorbic acid or alpha-tocopherol, buffer to retain the pH at an acceptable value including as an example potassium phosphate, preservative such as potassium sorbate or calcium propionate, silicone and other synthetic or natural polymers may also be added to the present composition in amounts that would not have an adverse effect on the activity of the composition as would be appreciated by one of skill in the art.

Uses of the Disclosed Compositions

A composition which can be applied, and adhere to, the tooth has many potential uses in dentistry. It can be used to seal areas of sensitive dentin; placed on the surface of sub-surface lesions and/or hypoplastic areas; used as a self applied occlusal sealant; and to treat and prevent erosion of teeth. Tooth erosion is the loss of mineral and organic material from enamel, dentin, or cementum caused by foods, drinks, topical agents of low pH or of a chelating nature. The ability of the composition to release fluoride, calcium, phosphate, and/or carbonate due to the fluctuation of pH in the oral environment allows for precipitation of calcium, phosphate, and/or fluoride at the site of application. Over time, these ions are then integrated into the tooth surface.

The release of ions from the apatite derivatives in the compositions disclosed herein at neutral or low pH can be used to combat dental caries, to remineralize the tooth surface, and/or to lessen tooth sensitivity. These properties may allow for better rebuilding and restoration of lost or diseased tissue.

Dentin sensitivity, or hypersensitivity, is a sharp, transient, well-localized pain in response to tactile, thermal, evaporative, or osmotic stimuli. This pain does not occur spontaneously and does not persist after removal of the stimuli. Dentin is an innervated tissue, and usually it is covered by enamel or cementum, once these protective non-innervated layers are lost and the tooth surface has exposed tubules to dentin, patients will start feeling sensitivity. The compositions disclosed herein can be used to treat or prevent tooth sensitivity. The apatite derivative crystals penetrate into the dentin tubules. The size of the crystals are preferably such that they can penetrate into the tubules. Tubules typically have a cross section of about 2 to about 3 μm, so crystals having a cross section less than 2 μm are preferred, and more preferably crystals of less than 1 μm, less than 500 nm, less than 400 nm, less than 300 nm, less than 200 nm, or less than 100 nm. In a highly preferred case, the crystals are about 20 to about 50 nm in cross section.

The compositions disclosed herein can adhere to wet or dry surfaces. For wet surfaces, a composition as disclosed herein can adhere to the surface, which precludes the necessity of drying the surface, e.g., the tooth surface, prior to the application of the composition. As used herein, the term "adhere" in this context, refers to the ability of at least a portion of the composition to remain in contact with a surface for at least 30 minutes, and more preferably at least 1 hour, at least 2 hours, at least 3 hours, or at least 4 hours to about 24 hours.

A water based composition allows the diffusion of ions, released by the oral pH fluctuations, from the apatite derivatives. These ions in turn diffuse into the dentin, and enamel, to help remineralize these surfaces. The apatite derivative crystals, which can be about 20 to about 50 nm in cross section, help block the dentin tubules directly where patent tubules are exposed in an area of sensitive dentin. A more permanent barrier is formed from minerals precipitated 'catalyzed' by ion release from the apatite derivate crystals onto the dentin surface and into the tubules.

One property of the disclosed compositions is that, when applied to the tooth, the apatite derivative crystals can penetrate into the dentin tubules of the tooth surface. By filling the tubules with the crystals of the compositions, the sensitivity of the teeth can be decreased. The ability of the compositions disclosed herein to adhere to the tooth surface allows the crystals sufficient time to interact with the tooth surface and thereby penetrate into the tubules of the tooth before being washed away by saliva or other means.

Another beneficial property of the disclosed compositions is that, under neutral and/or acidic conditions (i.e., pH less than 7), the FA or HA crystals can release calcium, phosphate, and/or fluoride ion. Thus, upon application to the tooth, the composition, which can be a paste-like consistency, will adhere to the tooth surface and, under neural and/or acidic conditions, provide fluoride, phosphate, and/or calcium ions. Over time, delivery of such ions directed to the tooth surface can allow for mineralization of the tooth surface.

The compositions disclosed herein, as pastes, can be applied to wet surfaces, such as human teeth, without the need for drying or special application techniques. Thus, the human can use these compositions at home. The compositions can be applied once a week, twice a week, once daily, twice daily, or three times daily, depending upon the need of the human for the apatite derivative of the composition. The application can be at convenient times, such as in the morning, or just prior to bed for overnight exposure. The timing and frequency of application of the compositions disclosed herein can readily be determined by the dentist professional.

In some cases, the compositions disclosed herein are used as a cosmetic tooth varnish. The composition is applied to the tooth and the white or white-like color of the composition gives the tooth the cosmetic appearance of whitening the tooth. Such compositions stay on the tooth surface in a temporary manner, such as less than 1 week, less than 5 days, less than 4 days, less than 3 days, less than 2 days, or up to one day. In such cases, the composition can further comprise a colorant that impacts the color of the composition, such as titanium dioxide other metal oxide, or other compound or additive deemed safe for use in the mouth. In some specific instances, the composition is tinted to a color other than white or off-white, for novelty purposes (e.g., black, green, blue, yellow, red, purple, orange).

Use of the Disclosed Resin Compositions

The resin compositions disclosed herein can be used in a variety of applications. In various cases, the resin compositions are used as dental restorative material. In some cases, the resin compositions are used in cements, sealants, sealers for root canal work, and/or as a base material for dental work. Materials comprising the resin compositions as disclosed herein exhibit a lower incidence of caries than materials that do not comprise the resin compositions as disclosed herein.

EXAMPLES

Additional aspects and details of the invention will be apparent from the following examples, which are intended to be illustrative rather than limiting.

Enamel-Like Paste Material Synthesis

Synthesis of FA crystals under ambient conditions has been described by Chen et al. *Crystal Growth Design.* 6:1504-1508 (2006) and WO 06/050365. Hydroxyapatite powder (104.6 mg) and 8.4 mg of sodium fluoride were mixed with 100 ml distilled water. The suspension was stirred continuously, and nitric acid was added until the powder dissolved, after which the pH was adjusted to 2.4. Ammonium hydroxide was then added drop wise to the solution with continuous stiffing until pH 6 was reached. The suspension was sealed in a plastic tube and kept in a water path at 70° C. for 2 days. Short FA nanorods were produced, which ranged between 20 and 100 nm and a cross section of approximately 10 to 20 nm. Transmission electron microscope (TEM), EDS and X-ray diffraction analysis (XRD) were used to assess the crystalline features.

Transmission Electron Microscopy (TEM)

A JEOL 3011 High Resolution Electron Microscope was used to examine the crystals' morphology, size, and crystalline structure. The crystal samples for TEM analysis were prepared by mixing with methanol and pipetted onto a holey-carbon film coated copper grids and dried. The prepped samples were then analyzed by TEM.

Fourier Transform Infrared Spectroscopy (FT-IR)

The infrared spectra of crystals are characterized by a PERKIN ELMER spectrum BX FT-IR system. The samples are prepared using a KBr pellet method, and the data taken using a scan number 8; scan range: 400-4000 $cm^{-1}$; and resolution 2 $cm^{-1}$.

X-Ray Diffraction Analysis (XRD)

The X-ray powder diffraction (XRD) patterns of the crystals for the determination of the profile breadth and relative intensity data will be collected from a Scintag X-1 Powder Diffraction using CuKa radiation refinement will be carried out on patterns to determine compositional effects on lattice parameters.

Sample Collection

Teeth were immersed in 70% ethyl alcohol for 24 hours, and then sectioned vertically at the center of the tooth in the mesial-distal plane. Any remnants of the pulp tissue were removed with the use of a dental excavator. Superficial layers of the cervical facial dentin were exposed with the use of a diamond saw while preserving the specimen in the wet state. Teeth were then stored in 0.9% saline solution. Teeth with extensive fillings or decay; signs of dentinogenesis imperfecta; obliterated or narrow pulp spaces (signs of aging) were excluded.

Scanning Electron Microscope (SEM)

Dentin sections were etched using 17% EDTA for 3 minutes to open the dentinal tubules and remove the obstructing smear layer (FIG. 1). Specimens were then rinsed with distilled water for 1 minute. Each section was then cut into two halves using a wire cutter (to prevent formation of a smear layer). The two sections were labeled, one as a test and the other section served as a control. The FA paste was applied to the wet dentin sections. The pastes were: 40% FA/Dopa in acetone (by volume), 40% FA/HEMA in ethanol (by volume), 20% FA/Alginate in water (by weight), respectively. The pastes were allowed to dry for 3 minutes before the excess removed from the dentin sections with the use of a flat metal spatula. The sections were then rinsed thoroughly with distilled water for 1 minute and left to dry. Afterwards, the test sections and their control counterparts were coated with gold for 60 sec (to an even thickness). The surface of the dentin was examined under SEM to demonstrate physical obstruction of the dentinal tubules by the paste. An estimated ratio for the open versus the obstructed dentinal tubules was recorded for each section. SEM analysis was conducted using a Hitachi S3200N Scanning Electron Microscope operated at 20 kV (resolution: 2.0 nm at 30 kV; 5.0 nm at 1 kV). A set of controls was established as follows:

1. Each of the gels without filler used was applied to a dentin section, left to dry for 3 minutes, the excess gel was removed from the surface, rinsed, gold coated, then examined under SEM.
2. Each of the gels applied to a dentin section, left to dry without removal or rinsing, gold coated and examined with SEM.
3. Dry FA crystals were applied to the dentin surface, gold coated, and examined with SEM.
4. FA crystals were mixed with water (40% by volume), left to dry for 3 minutes, removed with the flat metal spatula, rinsed with distilled water for 1 minute, gold coated, then examined with SEM.
5. 40% HA/HEMA was applied to etched dentin section, left to dry for 3 minutes, removed with the flat metal spatula, rinsed for 1 minute with distilled water, gold coated and examined Ion Release Measurement Fluoride concentration was measured with the use of an Orion combination fluoride electrode (available from Thermo Scientific, Waltham, Mass., USA), and calcium and phosphate analysis was determined by atomic absorption spectrometry or spectrophotometer.

The experiment was designed to mimic daily partial replacement of saliva in the mouth and the daily fluctuations of pH in the oral cavity after eating 3 meals per day. For that purpose; a control sample was prepared with 10 mg of FA nanorod crystals placed independently in scintillation vials with 10 ml of deionized water. Three times per day the pH of the water was reduced to pH 4.5 for 30 minutes using lactic acid and then returned to neutrality. Ca, P and F concentrations were measured at 25° C. by withdrawing 5 ml of the solution and mixing it with 5 ml TISAB II (Orion Research Incorporated, Boston, Mass.). Deionized water was added back to the vials to keep the specimen water volume at 10 ml. The same experiment was repeated for 3 test and 3 control samples. The test samples were: 40% FA/Dopa, 40% FA/HEMA, and 20% FA/Alginate. The control samples were: 25 µL Dopa, 25 µL HEMA, and 50 mg Alginate.

The second experiment was designed to mimic the overnight application of the disclosed composition. Square dentin sections of known surface area (3×3×1 mm) were cut and etched. 40% HEMA was applied to the dentin surface. The specimen was submerged in 10 mL deionized water. The solution was continuously stirred. Fluoride concentration was measured at baseline and after 8 hours.

Substrate Adhesion Test

Micro-tensile bond strength (uTBS) testing is used to evaluate the adhesion of compositions to dentin. A diamond wafering saw is used to section coronal dentin into bars (1 mm×1 mm×5.10 mm) using accepted techniques while preserving the specimen beams in the wet state. A polyethylene square trough is used to align two dentin-dentin ends to each other while placing paste between to produce a composite beam. The beam is cyanoacrylated to a Ciucchi specimen holder while maintaining the beam in a moist state. The test uses an EZ tester to produce specimen strain at 0.1 mm per minute while measuring the modulus and ultimate strength of the assembly. The modulus and strength of the composition is much lower than that of the other parts of the beam that they will govern the observed properties. The same test is used to evaluate the residual strength of pastes after varying lengths of time to monitor the general degradation of the carrying gel.

Figure 2:
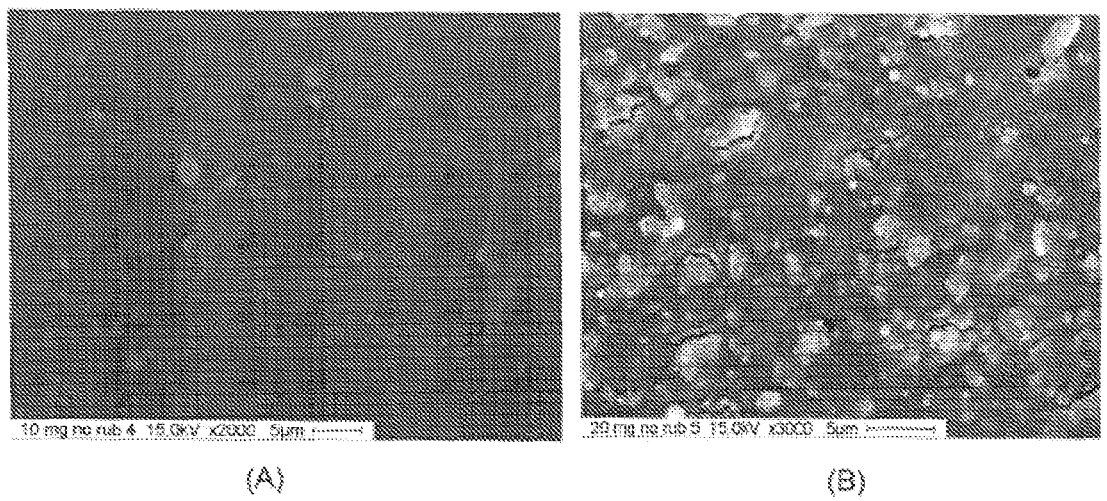
FIG. 2A shows SEM image of dentin surface after application of a 10 mg fluorapatite (FA) in 100 μL polymer composition, applied without rubbing.
FIG. 2B shows SEM image of dentin surface after application of a 20 mg FA in 100 μL polymer composition, applied without rubbing.
Figure 3:
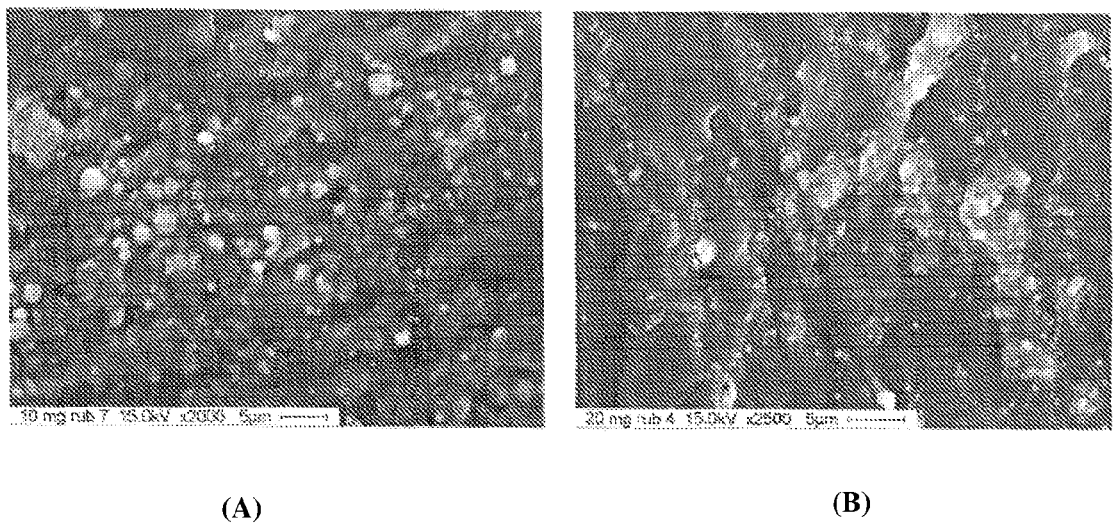
FIG. 3A shows SEM image of dentin surface after application of a 10 mg FA in 100 μL polymer composition, applied with rubbing for about 10 seconds.
FIG. 3B shows SEM image of dentin surface after application of a 20 mg FA in 100 μL polymer composition, applied with rubbing for about 10 seconds.

Two compositions (10 mg and 20 mg FA in 100 µL polymer) were applied to dentin surface both without (10 mg: FIG. 2A; 20 mg: FIG. 2B) and with rubbing for 10 seconds (10 mg: FIG. 3A; 20 mg: FIG. 3B). Rubbing of the paste on the tooth surface did not seem to contribute to penetration of the crystals into the tubules.

Preparation of a Resin Composition

An apatite derivative and a resin polymer are mixed together, optionally with stirring or vortexing, and optionally under vacuum, at a temperature of 25° C. to 50° C. to form the resin composition.

The subject matter described and claimed herein is not to be limited in scope by the specific embodiments provided. Functionally equivalent methods and components, in addition to those shown and described herein, will become apparent to those skilled in the art from the foregoing description and accompanying drawings. Such modifications are intended to fall within the scope of the appended claims. All references cited herein are hereby incorporated by reference in their entirety.

What is claimed:

1. A composition comprising fluorapatite crystals and a carrier, wherein the composition is capable of adhering to a wet or dry tooth surface.

2. The composition of claim 1, wherein the crystals have a length of about 500 nm to about 20 µm and a cross section of about 10 nm to about 500 nm.

3. The composition of claim 1, wherein the crystals have a length of about 1 to about 2 µm and a cross section of about 50 nm.

4. The composition of claim 1, wherein the fluorapatite is present in an amount of about 5 to about 60 wt %.

5. The composition of claim 1, wherein the carrier comprises a polymer, a surfactant, a lipid, or mixtures thereof.

6. The composition of claim 5, wherein the polymer comprises 2-hydroxyethyl methacryalte (HEMA), dihydroxyphenylalanine (DOPA), or alginate.

7. The composition of claim 6, wherein the polymer comprises HEMA.

8. The composition of claim 1, wherein the composition further comprises hydroxyapatite.

9. A resin composition comprising fluorapatite crystals and a resin polymer, wherein the resin polymer is selected from the group consisting of bisphenol A-glycidyl methacrylate (BIS-GMA), urethane dimethacrylate (UDMA), bisphenol A dimethacrylate (bis-DMA), ethylene glycol dimethacrylate (EGDMA), triethylene glycol dimethacrylate (TEGDMA), and mixtures thereof.

10. The resin composition of claim 9, wherein the crystals have a length of about 500 nm to about 2 µm and a cross section of about 50 nm to about 500 nm.

11. The resin composition of claim 9, wherein the fluorapatite is present in an amount of about 5 to about 60 wt %.

* * * * *

UNITED STATES PATENT AND TRADEMARK OFFICE
CERTIFICATE OF CORRECTION

PATENT NO.         : 8,765,168 B2  
APPLICATION NO.    : 13/505487  
DATED              : July 1, 2014  
INVENTOR(S)        : Brian H. Clarkson et al.

Page 1 of 1

It is certified that error appears in the above-identified patent and that said Letters Patent is hereby corrected as shown below:

In the Claims:

Column 10, line 43, Claim 6, "methacryalte" should be -- methacrylate --.

Signed and Sealed this
Twenty-first Day of July, 2015

Michelle K. Lee
*Director of the United States Patent and Trademark Office*